United States Patent
Torres Farr

(10) Patent No.: US 8,504,197 B2
(45) Date of Patent: Aug. 6, 2013

(54) VENDING MACHINE FOR DISPENSING FOODS AND THE LIKE

(76) Inventor: Elmer Sebastian Torres Farr, Tremestieri Etneo (IT)

( * ) Notice: Subject to any disclaimer, the term of this patent is extended or adjusted under 35 U.S.C. 154(b) by 146 days.

(21) Appl. No.: 12/927,771

(22) Filed: Nov. 22, 2010

(65) Prior Publication Data

US 2011/0125319 A1 May 26, 2011

(30) Foreign Application Priority Data

Nov. 23, 2009 (IT) ............................... MI2009A2048

(51) Int. Cl.
*G06F 17/00* (2006.01)

(52) U.S. Cl.
USPC ............................ 700/240; 700/233; 700/241

(58) Field of Classification Search
USPC .................................. 700/233, 239, 240, 241
See application file for complete search history.

(56) References Cited

U.S. PATENT DOCUMENTS

| | | | | |
|---|---|---|---|---|
| 2,836,980 | A | | 6/1958 | Giepen |
| 5,522,309 | A | * | 6/1996 | Mizobuchi et al. ............ 700/239 |
| 6,093,027 | A | | 7/2000 | Unger et al. |
| 7,122,005 | B2 | * | 10/2006 | Shusterman ........................ 221/2 |
| 7,295,889 | B2 | * | 11/2007 | Lahteenmaki ................ 700/233 |
| 7,451,015 | B2 | * | 11/2008 | Mazur et al. .................. 700/239 |
| 7,457,685 | B2 | * | 11/2008 | D'Silva .......................... 700/239 |
| 7,762,181 | B2 | * | 7/2010 | Boland et al. .................... 99/322 |
| 7,979,156 | B2 | * | 7/2011 | Ochi .............................. 700/240 |
| 2009/0125324 | A1 | | 5/2009 | Keravich et al. |

FOREIGN PATENT DOCUMENTS

| | | |
|---|---|---|
| CH | 141 714 A | 8/1930 |
| DE | 10 2007 017994 A1 | 10/2008 |
| EP | 1 327 965 A1 | 7/2003 |
| JP | 2001 093031 A | 4/2001 |
| JP | 2003 217010 A | 7/2003 |
| WO | WO 02/25608 A1 | 3/2002 |

* cited by examiner

*Primary Examiner* — Timothy Waggoner
(74) *Attorney, Agent, or Firm* — R. Ruschena Patent Agent, LLC

(57) ABSTRACT

It is provided a vending machine (1) for dispensing foods and the like, comprising at least one food dispenser (2) adapted to hold and dispense foods to a user, and an evaluation system (3) suitable to evaluate the user's body condition and select one of the foods, based on said evaluation.

6 Claims, 1 Drawing Sheet

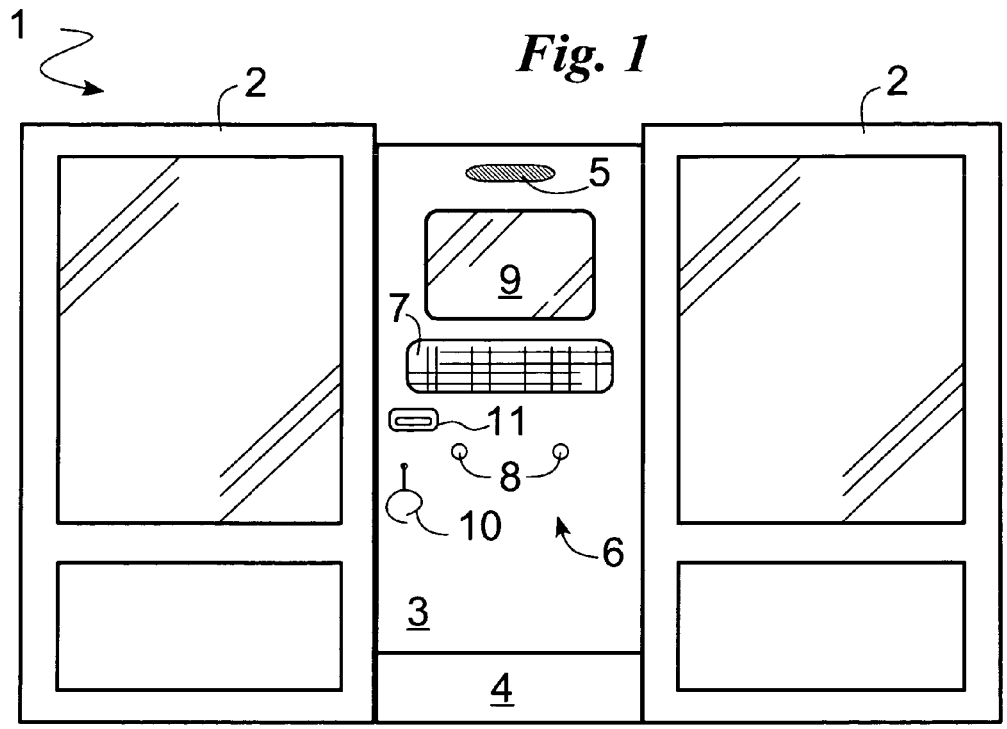
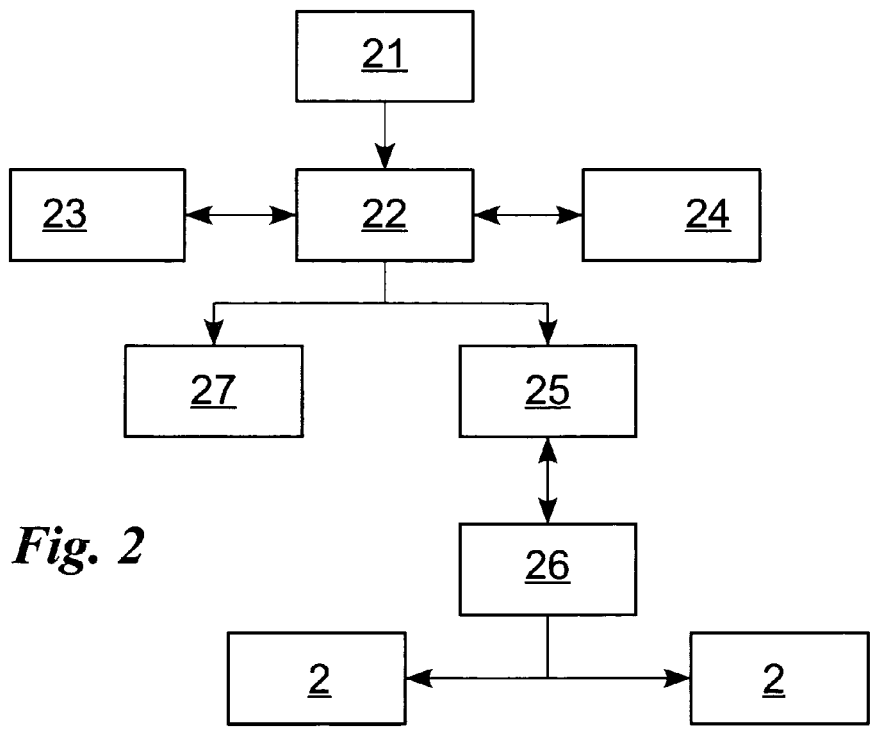

VENDING MACHINE FOR DISPENSING FOODS AND THE LIKE

FIELD OF THE INVENTION

The present invention relates to a vending machine for dispensing foods and the like of the type pointed out in the preamble of the first claim.

It is known that presently there are on the market vending machines for dispensing foods, which are adapted to provide the user with foods of any type such as snacks, hot or cold drinks.

By the term snack it is intended a light and quick small meal eaten between the traditional main meals, that is to say breakfast, lunch and dinner. Its nutritional function is to give energy in order to avoid drops in attention and good mood that physiologically occur in postprandial periods, such as late in the morning and in the afternoon.

In particular, a snack must fulfil the energetic function by a suitable introduction of nutritional substances ensuring the best effect on the state of attention and cognitive performance.

For this reason vending machines for dispensing foods are installed in well-attended places, i.e. places characterised by a good presence of people where however no refreshment rooms are provided, such as stations, airports, schools, gymnasiums and public libraries.

DESCRIPTION OF THE PRIOR ART

Vending machines supply a series of goods that are classified based on their arrangement inside said machine; therefore the consumer selects the goods through an alphanumeric keyboard, depending on his/her taste and wishes. In particular, this choice is carried out by typing, through said keyboard, the code identifying the goods position.

This choice is therefore made by the consumer based on his/her taste and wishes, without taking into due account the nutritional values of the selected goods or products, and consequently does not follow the rules of a correct diet, which means that the food is not selected based on its supply of nutritional substances.

To be considered among the most important nutritional substances are proteins, fats and carbohydrates.

Proteins represent the fundamental constituents of each body cell and lack of them leads to hypotrophy of the muscular masses, asthenia, difficulty in concentration, libido reduction, while an excess of animal proteins, which is presently rather common, leads to metabolism disorders, arthritic troubles, cardiovascular diseases, premature ageing.

Fats, also called lipids, in the human organism perform a caloric function and therefore constitute an energy supply which the organism turns to, in case of need. Fats in their form of essential fatty acids fulfil very important functions, for example for conveying lipids to the blood. Therefore, in addition to the depot fat there is an active fat that is continuously used and renewal of which through the food is required, and consequently a healthy diet must supply a certain amount of fats.

No syndromes due to lack of fats are known, given their diffusion in the most common foods; it is however to be pointed out that in case of lack of polyunsaturated fatty acids, troubles concerning the skin can occur with premature skin withering.

Finally, carbohydrates also referred to as sugars or glucides, are the food components designed to supply ready energy; as soon as they are introduced into the organism, they are used as fuel for all organic processes; however if there is an excessive supply of same, they can be converted into fats and be deposited, as it happens in obesity.

Under conditions of a deficient introduction of carbohydrates, as it often happens during a slimming diet, use of the depot fats as an energy source takes place, however with occurrence of an acetonemia condition, due to the incomplete combustion of lipids.

One of the most important and frequent problems connected with a wrong supply of fats and carbohydrates is an overweight condition that in the most extreme cases becomes obesity.

Obesity and overweight are conditions associated with premature death and are now universally recognised as factors of risk for the main chronic illnesses: cardiovascular diseases, ictus, diabetes, gall bladder diseases, osteoarthritis or some types of tumours, such as endometrium, colon-rectum and kidney tumours, gall bladder tumours and mamma tumours in post-menopausal.

Other health problems associated with an excessive body weight are: hypertension, hypercholesteremia, night apnea and respiratory troubles, asthma, increased surgical risks, complications during pregnancy, hirsutism and irregularities in the menstrual cycle.

The population classification based on weight is made using several indexes, one of which is the index of the body mass (BMI=Body Mass Index), which is considered as the most representative index of the presence of body fat in excess. The BMI is calculated using the ratio between the weight, expressed in kg, and the height, expressed in m, according to the following formula:

$$BMI = weight/height^2$$

The weight classes stated by the body mass index are: under weight if the BMI is lower than 18.5; normal weight if the BMI is included between 18.5 and 24.9; over weight if included between 25 and 29.9 and obesity if the BMI exceeds 30. Finally, there are differences connected with the sex; for instance the BMI being the same, women tend to have a greater amount of body fat as compared with men, in the same manner as old people compared with young people. In addition, a person having a sports physique may have a higher weight, exactly due to the very developed muscular mass, although not falling for this reason within the overweight or obesity category.

Therefore the food choice depends on a lot of factors, such as age, height, weight, type of life, i.e. sedentary or not, physical activity; it is therefore apparent that this choice is complex and very peculiar, as it depends on the consumer's particular physical and habitual features.

In addition, the user is unable to known the composition of the foods contained in the vending machine and therefore he/she can unwarely select foods containing ingredients adapted to give rise to physical problems such as those due to allergies or food intolerances.

It is therefore important to have a vending machine capable of supplying the user with the food that, among those present inside it, is the most appropriate to his/her particular requirements.

SUMMARY OF THE INVENTION

This aim is reached by a vending machine for dispensing foods and the like as claimed in the appended Claim 1.

Preferred embodiments are highlighted in the sub-claims.

The features and advantages of the invention are hereinafter clarified by the detailed description of a preferred embodiment of the invention, with reference to the accompanying drawings.

BRIEF DESCRIPTION OF THE DRAWINGS

The attached drawings show, by way of example, the preferred embodiments of the invention, in particular:

FIG. 1 shows a view of the vending machine for dispensing foods and the like;

FIG. 2 is a block diagram showing the operation of the machine.

With reference to the drawing, the vending machine for dispensing foods and the like according to the invention is generally identified by reference numeral 1.

It comprises at least one food dispenser 2 suitable to hold and distribute snacks, drinks and other foods, and an evaluation system 3 adapted to carry out an evaluation of the user's body condition. By "body condition" it is intended an estimate of the user's nutritional state, such as the percentage of his/her fat mass relative to the lean mass, based on the user's physical and habitual features.

The food dispensers 2 are preferably two in number: one holding drinks and one holding snacks or solid foods in general; in addition the two dispensers 2 are advantageously spaced apart from each other so as to enable the evaluation system 3 to be housed between said two dispensers 2.

System 3 comprises at least one of the following components: weighing scales 4, an instrument 5 able to measure the user's height, an element 6 suitable to determine the body composition, or an input device 7 adapted to enable personal data to be inputted to said machine.

In particular, system 3 comprises a combination of the aforesaid components and preferably it comprises all the previously listed components.

The evaluation system 3 allows the vending machine 1 to suggest the most appropriate food based on the user's body condition which is evaluated through suitable parameters, such as BMI, weight, height and age.

This evaluation is therefore carried out based on physical parameters that can be inputted by the user himself/herself or measured by the evaluation system 3 through the aforesaid components.

The weighing scales, adapted to measure the user's weight, are placed in such a manner as to make their use easy and are therefore advantageously disposed close to the lower part of one of the dispensers. In particular, the scales 4 are located between the two dispensers 2, as shown in FIG. 1.

Suitably positioned above the scales 4 is element 6 which is adapted to measure the composition of the body mass, therefore evaluating the presence and amount both of the fat mass and the lean mass.

Said measurement can be carried out following different techniques, one of the most important of them being the bioimpedance, in which the presence of fat mass and lean mass is estimated based on the different opposition of the various tissues when passage of current takes place.

In order to create said passage through the user's body, element 6 comprises at least one electrode 8. Preferably, the electrodes 8 are two in number and are such disposed as to enable the user to easily put a finger in each of the two electrodes 8.

Instrument 5 is adapted to measure the user's height and can be an anthropometer consisting of a graduated rod along which a slider runs, i.e. an element adapted to be laid on the user's head so as to enable his/her height to be determined.

Alternatively, it consists of instruments adapted to automatically detect the user's height, such as optical instruments for example.

Finally, an input device 7 is provided which is adapted to enable data relating to the user, such as the age, to be inputted in an automatic or manual manner.

Device 7 can allow the user to input, in addition to physical data, also medical data, such as those connected with a diet being followed or concerning allergies or food intolerances, or still other data such as those concerning an only just performed physical activity and the type of life, for example sedentary or with much sport.

Finally, it also enables data concerning the preceding meals to be inputted into the evaluation system 3 so that said system 3 is allowed to make a choice adapted to provide the proper supply of substances in the whole day and not for the individual meal.

This device 7 can be made up of an alphanumeric keyboard, a display of the touch-screen type, or a device suitable to read magnetic cards and bar codes.

A further instrument with which the evaluation system 3 can be equipped is the apparatus 10 for measurement of the bone thickness. Said apparatus is suitable to measure the wrist circumference, in such a manner as to determine the bone structure, i.e. the size of the user's bones.

Finally, the evaluation system 3 can be further provided with a display 9 adapted to enable the user to verify whether the inputted data are correct and to know information concerning the foods present in the dispensers 2, such as price and ingredients, for example.

Display 9 is also suitable to provide a nutritional report, i.e. the final data concerning the body evaluation of the individual. This report can be at last printed through a printer 11 which is preferably placed in the evaluation device in the vicinity of the input device 7.

Operation of the vending machine 1 for dispensing foods and the like described above as regards structure is the following.

The user gets on the scales 4 that measure his/her weight while simultaneously instrument 5 determines the user's height.

Subsequently or simultaneously, the user puts his/her hands in contact with element 6 so as to calculate his/her body composition, in particular he/she puts a finger of each hand in contact with an electrode 8.

In addition, through the apparatus for measurement of the bone thickness 10, the user measures the circumference of his/her wrist. Finally the remaining data are inputted through the input device 7.

The previously described sequence of operations that is adapted to provide the vending machine 1 with data concerning the user, does not contemplate a single succession, but the operations can be carried out in a random manner.

Based on the data provided by the user and those related to the foods contained in the dispenser, the vending machine 1 selects and proposes or delivers the most appropriate food.

It should be pointed out however that this choice can only have an indicative character and therefore the user is free to also choose a food different from that suggested by the machine 1.

Operation of the machine is shown in the block diagram in FIG. 2.

First the inputs 21 are entered, i.e. the previously described data such as weight and height, for example.

These inputs 21 are then processed by a central processing unit 22, in particular a computer based on a data base 23 with medical information and the list of the available foods 24 in which the ingredients and nutritional values of the foods are described. In particular, in addition to the above information, the list also contains suggestions for information purposes only, such as the physical activity to be done for digesting each food.

Advantageously, the central unit 22 supplies a nutritional report 27 in which the results of the body evaluation such as the BMI and body composition are reproduced. The report 27 therefore contains a final evaluation of the user's physical state. In particular, the data base 23 contains the information adapted to evaluate the user's body condition, such as the BMI or other medical parameters like those relating to food intolerances or allergies.

Said central unit 22 provides a list of the appropriate foods 25, i.e. a list of the goods that have been judged as suiting the user's requirements. This list 25 is examined by the user who makes a choice 26 from the foods present in said list 25 or, if it is so wished by the user, from any other product present in the dispensers 2.

Finally a central unit 22 adapted to contain the historical data of a user may be provided, thus enabling the user physical course to be examined and therefore a long-term programming of his/her diet to be done.

The invention enables important advantages to be achieved.

In fact, the machine 1 allows automatic identification of the optimal food among those contained in the dispensers 2, based on the user's particular physico-medical requirements.

The machine 1 provides the user with the most appropriate food for his/her diet or the performed physical activity; for instance, it selects the most appropriate food for restoring the substances and fluids lost during said physical activity.

In addition, the vending machine 1 can be used not only for dispensing snacks or drinks for a light meal, but also for giving the user a complete meal. Therefore, the vending machine 1 can be used in service centres such as hospitals or welfare centers where an accurate choice of the food based on the user's state of health is necessary.

The possibility of having nutritional information on the product and suggestions on the physical activity to be done for digesting the food makes the evaluation system able to suggest a food only based on the physical activity performed by the user.

The invention is susceptible of variations all falling within the inventive idea.

All of the details can be replaced by equivalent elements and the materials, shapes and sizes can be of any nature and magnitude.

What I claim is:

1. A vending machine (1) for dispensing foods and the like comprising at least one food dispenser (2) designed to hold and distribute said foods to a user, said vending machine (1) comprises an evaluation system (3) suitable to carry out an evaluation of the current body condition of a user and select at least one of said foods based on said evaluation; said evaluation system (3) comprises:
    weighing scales (4) to measure the user's current weight;
    an instrument (5) able to measure the user's current height;
    a measuring element (6) designed to determine the user's current body composition;
    an apparatus for measuring the user's bone thickness (10) to enable it to determine the user's bone structure.

2. A vending machine (1) according to claim 1, wherein said evaluation system (3) is suitable to select a list of said foods based on medical and personal current data of said user and nutritional information on the ingredients of said foods.

3. A vending machine (1) according to claim 1, wherein said evaluation system (3) comprises a central process unit (22) that, based on a database (23) of medical information and a list of the available foods (24), provides a list of suitable products (25) and a nutritional report (27) to said user.

4. A vending machine (1) according to claim 1, wherein said instrument (5) is of optical type.

5. A vending machine (1) according to claim 1, wherein said element (6) comprises at least one electrode (8) adapted to come into direct contact with at least one portion of said user's upper limb.

6. A vending machine (1) according to claim 1, wherein said evaluation system (3) further comprises an input device (7) suitable to enable data relating to said user to be inputted to said vending machine (1).

* * * * *